United States Patent [19]

Bird et al.

[11] 4,238,420

[45] * Dec. 9, 1980

[54] PRODUCTION OF HEXANITROSTILBENE USING INORGANIC BUFFERS

[75] Inventors: Roger Bird, Swindon; Allen E. Webb, Waltham Abbey, both of England

[73] Assignee: The Secretary of State for Defence in Her Britannic Majesty's Government of the United Kingdom of Great Britain and Northern Ireland, London, England

[ * ] Notice: The portion of the term of this patent subsequent to Dec. 9, 1997, has been disclaimed.

[21] Appl. No.: 17,972

[22] Filed: Mar. 6, 1979

[30] Foreign Application Priority Data

Mar. 7, 1978 [GB] United Kingdom ............... 9077/78

[51] Int. Cl.$^3$ ............................................. C07C 79/10
[52] U.S. Cl. ................................................... 568/931
[58] Field of Search ...................................... 260/645

[56] References Cited

U.S. PATENT DOCUMENTS

| | | | |
|---|---|---|---|
| 3,505,413 | 4/1970 | Shipp | 260/645 |
| 4,085,152 | 4/1978 | Salter et al. | 260/645 |

Primary Examiner—Benjamin R. Padgett
Assistant Examiner—Deborah L. Kyle

Attorney, Agent, or Firm—Stevens, Davis, Miller & Mosher

[57] ABSTRACT

The yield of hexanitrostilbene from the reaction of 2,4,6-trinitrotoluene and an alkali metal or alkaline earth metal hypochlorite, in an aqueous organic solvent, is improved by adjusting the pH of the reaction mixture to within the range 9.5 to 11.0 and then maintaining the pH within that range by the addition of an inorganic buffer. The pH is preferably kept above 9.75, especially from 10 to 10.5.

In a preferred embodiment, 2,4,6-trinitrotoluene is contacted with aqueous sodium hypochlorite (containing from 4 to 10% (w/v chlorine) in tetrahydrofuran-methanol. After an initial reaction period of between 0.5 to 3 minutes, an inorganic acid, especially sulphuric or hydrochloric acid is added to the reaction mixture to bring its pH within the required range, and then an inorganic buffer, especially sodium carbonate-sodium bicarbonate, is added to maintain the pH within that range. The controlled reaction proceeds for 1 to 2 hours at $-5°$ to $25°$ C., preferably $10°$ to $16°$ C. During this time the reaction mixture need not be stirred. This minimizes the break up of the solid product and facilitates the filtration and washing of the hexanitrostilbene. Well-known methods of isolation then afford hexanitrostilbene in yields of about 50%.

15 Claims, No Drawings

PRODUCTION OF HEXANITROSTILBENE USING INORGANIC BUFFERS

The present invention relates to the production of 2,2',4,4',6,6'- hexanitrostilbene.

U.S. Pat. No. 3,505,413 describes a process for the production of 2,2',4,4',6,6'-hexanitrostilbene which comprises reacting in an organic solvent, 2,4,6-trinitrotoluene with an alkali metal or alkaline earth metal hypochlorite. U.S. Pat. No. 4,085,152 describes and claims an improvement thereon wherein the yield is increased by subsequently adding a nitrogenous base to the reaction mixture. The base typically is an organic amine or, to counteract the base released in the process, an amine hydrochloride. These materials are unpleasant to handle and although their presence is beneficial to the reaction in terms of yield, an alternative to their use has been sought.

Accordingly the present invention avoids the use of nitrogenous base and instead provides a process for the production of 2,2',4,4',6,6'-hexanitrostilbene which comprises contacting, in an aqueous organic solvent, 2,4,6-trinitrotoluene with an alkali or alkaline earth metal hypochlorite and at least after an initial reaction period, adjusting the pH of the reaction mixture to within the range 9.5 to 11.0 and then maintaining the pH of the reaction mixture within that range by the addition of an inorganic buffer. The pH is preferably kept above 9.75, especially from 10 to 10.5.

The initial reaction period will, as explained in U.S. Pat. No. 4,085,152 normally be within the range 0.5 to 3 minutes. The aqueous organic solvent should preferably contain 40–50% (by weight) of water. In general the major proportion of the water content will be provided by an aqueous hypochlorite solution and an aqueous solution of inorganic buffer, although water may also be introduced with, for example, the organic component. The organic component of the solvent may, for example, be dioxan, diglyme, or acetonitrile or mixtures thereof, but is preferably a mixture of tetrahydrofuran with another solvent especially methanol.

As the initial (rapid) reaction of the hypochlorite with the trinitroluene to give trinitrobenzyl chloride releases hydroxide ions it has been found that in order to obtain an optimum yield, acid should be added at this stage to give a pH within the required range. Preferably the acid is an inorganic acid such as sulphuric or hydrochloric acid. The pH is then maintained during the subsequent (slow) conversion of the trinitrobenzyl chloride to the hexanitrostilbene product (which process takes up hydroxide ions) by addition of the inorganic buffer which may be added in one stage or progressively, either continuously or batchwise. In this way the pH may be kept at or around the optimum valve for the reaction throughout its course. The inorganic buffer may be any inorganic buffer system soluble in the aqeuous organic solvent mixture used and capable of buffering within the desired pH range. Examples include borax/boric acid and especially carbonate/bicarbonate buffers. Preferably the inorganic buffer is a sodium carbonate/sodium bicarbonate buffer.

In one technique for carrying out the process according to the invention the reactants, 2,4,6-trinitrotoluene and the alkali or alkaline earth metal hypochlorite, are mixed in an aqueous organic solvent in a reactor. Acid is run into the reactor effluent to bring its pH down to the desired level and the whole mixture is drained into a tank. The pH of the liquid in the tank can be checked by means of a suitable electrode and inorganic buffer can be run into the tank as required to compensate for the increasing acidity of the reaction mixture caused by the progressive conversion to hexanitrostilbene product.

It will be apparent that as the final reaction to hexanitrostilbene nears completion the rate of addition of inorganic buffer which is necessary to ensure a constant pH will also decline and the pH will cease to change after completion of the reaction. In practice due to the slowness of the reaction it may be preferred to stop the process somewhat before the reaction is fully complete. A reaction time of from one to two hours has been found to be normally suitable.

A particular advantage of this process is that, after the addition of the buffer, the reaction mixture need not be stirred during the reaction. The absence of stirring minimises the break up of the solid product during the reaction and facilitates the filtration and washing of the hexanitrostilbene.

The entire reaction is preferably carried out at a temperature within the range −5° to 25° C., most preferably from 10° to 16° C. After completion of the reaction, the suspension obtained is filtered to separate the product. This may be washed with acetone and water (or with aqueous acetone) to remove impurities. Yields of up to about 50% of hexanitrostilbene are obtainable by this process.

The process of the invention will now be further described by way of example, by reference to some specific procedures, using apparatus similar to that illustrated in U.S. Pat. No. 4,085,152,

EXAMPLE 1

500 g of 2,4,6-trinitrotoluene was dissolved in 6.38 liter of solvent and this solution was mixed with 3.5 liter of hypochlorite feedstock (5.8% w/v free chlorine) in a stirred continuous reactor fitted with a cooling coil to remove the heat of reaction. The residence time in the reactor was of the order of 1.5 minutes and the pH of the reactor effluent was on average about 12.

The effluent was pumped from the reactor and mixed with dilute (25%) sulphuric acid to bring its pH within the range 10 to 10.2. This reaction mixture was then run into an ageing vessel to which, at two minute intervals, was added six equal portions of a solution of 220 g of anhydrous sodium carbonate and 43.5 g of anhydrous sodium bicarbonate in 1100 ml of water. In this way an even addition of buffer to the solution in the ageing vessel was obtained. On an average run, the pH of the reaction mixture plus the buffer was within the range 10 to 10.2 immediately after the addition of the final aliquot of buffer, and then dropped to pH 9.5 after 90 minutes.

In order to minimise the break up of the hexanitrostilbene caused by stirring, the liquors were not stirred during the run. At the end of the run the liquor in the ageing vessel was stirred very gently for about 5 seconds.

The final product was collected by acidifying the reaction mixture, filtering off the product in suspension and washing the collected solid with, consecutively, acetone and water. The hexanitrostilbene obtained was finally dried and weighed. The yield of HNS was 48.5%.

EXAMPLE 2

16 kg. of 2,4,6,-trinitrotoluene was dissolved in 204 liters of solvent and reacted with 116 liters of sodium hypochlorite solution as in Example 1. The reactor overflow was mixed with sufficient 50% sulphuric acid to maintain the pH of the reaction mixture at 10.2 (approximately 3 liters of acid required). This reaction mixture was then run into an ageing vessel where the buffer solution of 3 Kg. sodium carbonate, 1 Kg. sodium bicarbonate in 34 liters of water was added at a rate proportional to the reactor flow rate.

In order to minimise the break up of the hexanitrostilbene in the buffered reaction mixture, the liquors in the ageing vessel were not stirred. After standing for 2 hours, the liquors were acidified with 40 liters of 50% sulphuric acid and the final product collected, in 45% overall yield, by the process outlined in Example 1.

We claim:

1. A process for the production of 2,2',4,4',6,6'-hexanitrostilbene which comprises contacting in an aqueous organic solvent, 2,4,6-trinitrotoluene with an alkali or alkaline earth metal hypochlorite and, at least after an initial reaction period, adjusting the pH of the reaction mixture to within the range 9.5 to 11.0 and then maintaining the pH of the reaction mixture within that range by the addition of an inorganic buffer.

2. A process according to claim 1 wherein the inorganic buffer is a carbonate-bicarbonate buffer.

3. A process according to claim 2 wherein the inorganic buffer is a sodium carbonate-sodium bicarbonate buffer.

4. A process according to claim 1 wherein the inorganic buffer is a borax-boric acid buffer.

5. A process according to claim 1 wherein the pH of the reaction mixture is adjusted to and maintained within the range 9.75 to 11.0.

6. A process according to claim 5 wherein the pH of the reaction mixture is adjusted to and maintained within the range 10 to 10.5.

7. A process according to claim 1 wherein the pH of the reaction mixture is adjusted to within the said range by addition of an inorganic acid.

8. A process according to claim 7 wherein the acid is selected from sulphuric acid and hydrochloric acid.

9. A process according to claim 1 wherein the initial reaction period is within the range 0.5 to 3 minutes.

10. A process according to claim 1 wherein the inorganic buffer is added progressively during the reaction.

11. A process according to claim 1 wherein the aqueous organic solvent comprises water and a mixture of tetrahydrofuran and methanol.

12. A process according to claim 1 wherein the hypochlorite comprises sodium hypochlorite.

13. A process according to claim 1 wherein the hypochlorite is added as an aqueous solution having a concentration of free chlorine within the range 4 to 10% (w/v).

14. A process according to claim 1 wherein the reaction is carried out at a temperature within the range $-5°$ to $25°$ C.

15. A process according to claim 1 wherein the reaction is carried out at a temperature within the range $10°$ to $16°$ C.

* * * * *